(12) United States Patent
Worthley

(10) Patent No.: US 6,998,511 B2
(45) Date of Patent: Feb. 14, 2006

(54) DRESSING AND A METHOD FOR APPLYING THE SAME

(75) Inventor: George Worthley, Wheaton, IL (US)

(73) Assignee: George Medical, Wheaton, IL (US)

( * ) Notice: Subject to any disclaimer, the term of this patent is extended or adjusted under 35 U.S.C. 154(b) by 0 days.

(21) Appl. No.: 10/834,704

(22) Filed: Apr. 29, 2004

(65) Prior Publication Data

US 2004/0220505 A1 Nov. 4, 2004

Related U.S. Application Data

(60) Provisional application No. 60/467,715, filed on May 3, 2003, provisional application No. 60/479,597, filed on Jun. 19, 2003.

(51) Int. Cl.
*A61F 13/00* (2006.01)

(52) U.S. Cl. .............................. 602/57; 602/41; 602/42; 602/43

(58) Field of Classification Search ............ 602/41–43, 602/52, 57, 59; 604/179, 180; 128/877, 128/878, 879
See application file for complete search history.

(56) References Cited

U.S. PATENT DOCUMENTS

| | | | |
|---|---|---|---|
| 4,324,237 A | 4/1982 | Buttaravoli | |
| 4,485,809 A | 12/1984 | Dellas | |
| 4,534,762 A | 8/1985 | Heyer | |
| 4,598,004 A | 7/1986 | Heinecke | |
| 4,641,643 A * | 2/1987 | Greer | 128/888 |
| 4,664,106 A | 5/1987 | Snedeker | |
| 4,669,458 A | 6/1987 | Abraham et al. | |
| 4,678,462 A | 7/1987 | Vaillancourt | |
| 4,753,231 A | 6/1988 | Lang et al. | |
| 4,875,473 A | 10/1989 | Alvarez | |
| 4,917,112 A * | 4/1990 | Kalt | 602/58 |
| 4,919,654 A | 4/1990 | Kalt | |
| 4,926,850 A | 5/1990 | Lott et al. | |
| RE33,353 E | 9/1990 | Heinecke | |
| 4,966,590 A | 10/1990 | Kalt | |
| 4,973,314 A | 11/1990 | Garrett | |
| 5,000,741 A | 3/1991 | Kalt | |
| 5,074,293 A | 12/1991 | Lott et al. | |
| 5,074,847 A | 12/1991 | Greenwell et al. | |
| 5,088,483 A * | 2/1992 | Heinecke | 602/46 |
| 5,092,323 A | 3/1992 | Riedel et al. | |
| 5,106,629 A | 4/1992 | Cartmell et al. | |
| 5,282,791 A | 2/1994 | Lipton et al. | |
| 5,372,589 A * | 12/1994 | Davis | 604/180 |
| 5,380,294 A | 1/1995 | Persson | |
| 5,520,629 A | 5/1996 | Heinecke et al. | |
| 5,658,629 A * | 8/1997 | Delcuve et al. | 428/41.3 |
| 5,738,642 A | 4/1998 | Heinecke et al. | |
| 5,776,106 A | 7/1998 | Matyas | |
| 5,885,254 A | 3/1999 | Matyas | |
| 5,980,497 A | 11/1999 | Yavitz | |
| 6,124,520 A * | 9/2000 | Roberts | 602/54 |

(Continued)

Primary Examiner—Kim M. Lewis
(74) Attorney, Agent, or Firm—Patents + TMS, P.C.

(57) ABSTRACT

A dressing and a method for applying the same to a catheter entry site are provided. The dressing may have a transparent film within the dressing which may allow an individual to view, for example, a catheter entry site, or a wound on a patient. A portion of the transparent film may be free from adhesive, which may enable the dressing to be removed from the catheter entry site without inadvertent adhesion of the film to the patient and/or a catheter. Further, the dressing may be flexible and may contour to a shape of a catheter to prevent contaminants from entering the site.

27 Claims, 1 Drawing Sheet

U.S. PATENT DOCUMENTS

| | | | |
|---|---|---|---|
| 6,124,521 A * | 9/2000 | Roberts | 602/54 |
| 6,149,614 A | 11/2000 | Dunshee et al. | |
| 6,264,976 B1 | 7/2001 | Heinecke et al. | |
| 6,436,432 B1 | 8/2002 | Heinecke et al. | |
| 6,461,467 B1 | 10/2002 | Blatchford et al. | |
| 6,706,940 B1 | 3/2004 | Worthley | |
| 6,841,715 B1 * | 1/2005 | Roberts | 602/54 |
| 2002/0107466 A1 | 8/2002 | Faasse, Jr. | |
| 2002/0115954 A1 * | 8/2002 | Worthley | 602/57 |
| 2002/0123710 A1 * | 9/2002 | Worthley | 602/54 |
| 2002/0169405 A1 | 11/2002 | Roberts | |
| 2004/0059273 A1 * | 3/2004 | Worthley | 602/54 |
| 2004/0077984 A1 * | 4/2004 | Worthley | 602/55 |
| 2004/0143220 A1 * | 7/2004 | Worthley | 604/174 |

* cited by examiner

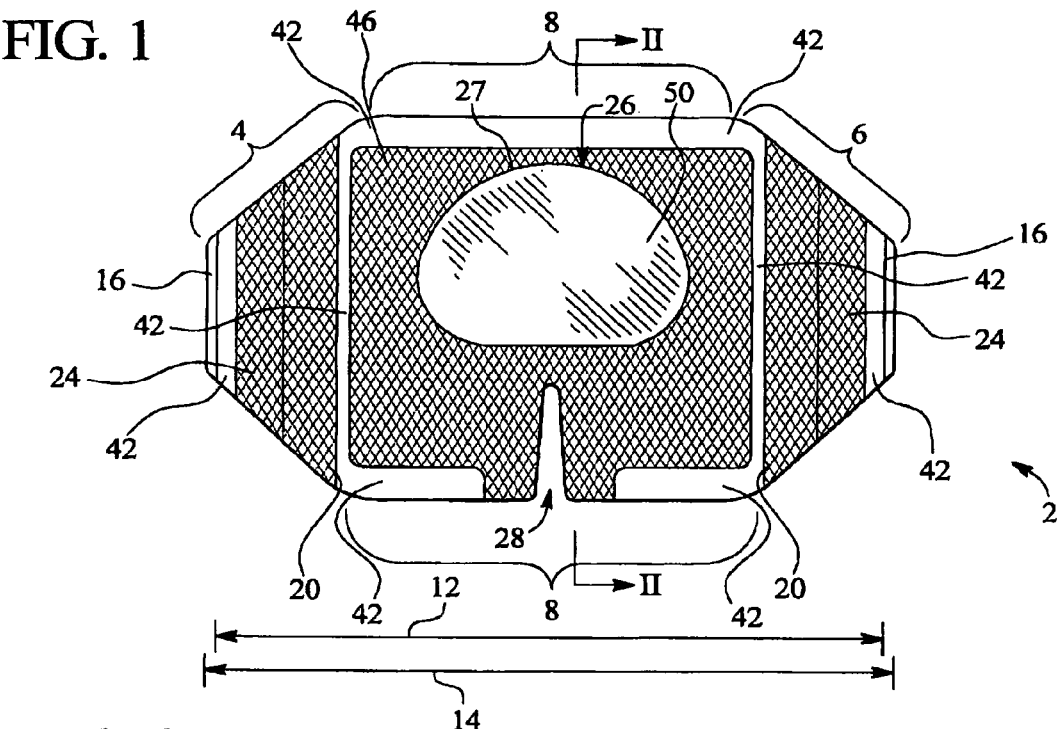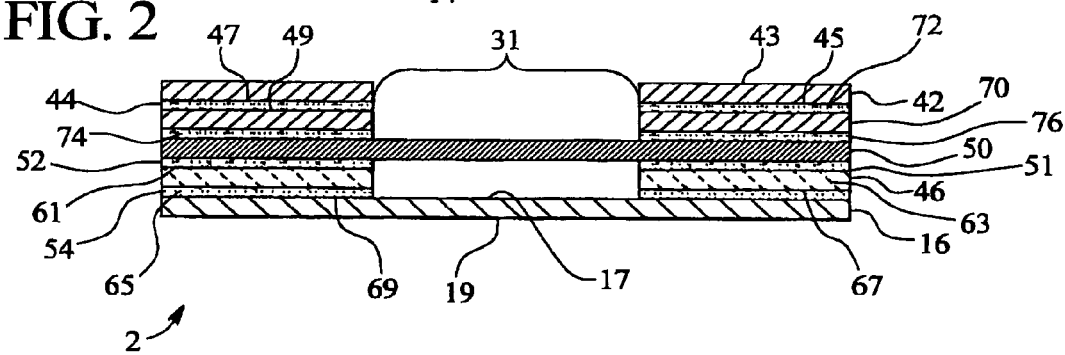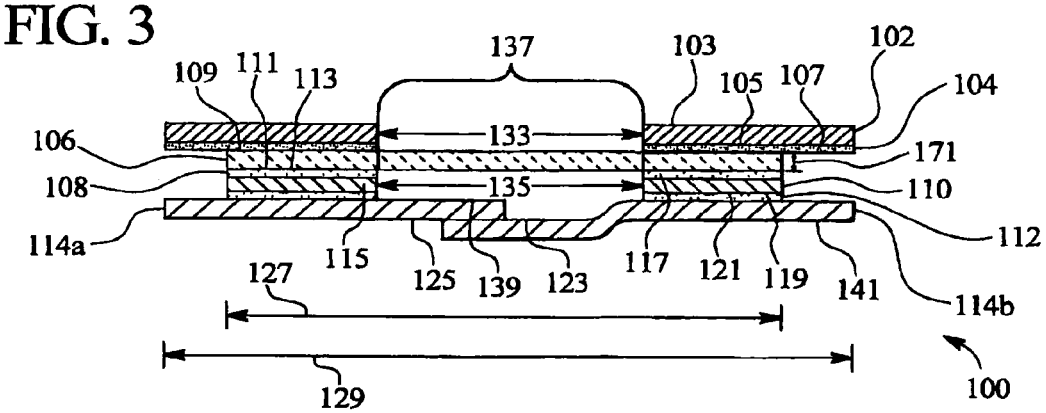

DRESSING AND A METHOD FOR APPLYING THE SAME

This application claims the benefit of U.S. Provisional Application Ser. No.: 60/467,715, filed May 3, 2003 and U.S. Provisional Application Ser. No.: 60/479,597, filed Jun. 19, 2003.

BACKGROUND OF THE INVENTION

The present invention generally relates to a dressing which may be applied at an intravenous catheter site of a patient as well as a method for applying the same. More specifically, the present invention relates to a dressing which may have a window or transparent film within the dressing. While the dressing may have an adhesive layer, no adhesive is present on the window. As a result, the dressing applied to the site may be removed without adhesion of the window to the patient and/or a catheter.

It is, of course, generally known to use dressings for the treatment and/or covering of wounds and intravenous catheter sites. Wound dressings that adhere to human skin by pressure-sensitive adhesive have been known for many years. Such dressings are generally in the form of a sheet of film, foam, fabric or combination thereof. Known sheets have a pressure-sensitive adhesive layer for adhering the dressing to skin adjacent to the wound to secure the dressing in place. The pressure-sensitive adhesive layer may be configured to adhere to the skin surrounding the wound or to portions of skin surrounding the wound. In many dressings, the adhesive layer is substantially coextensive with the dressing and thus extends over the wound itself. In such dressings, the adhesives are intended to adhere to healthy skin outside the wound but not to the wound itself. The adhesives do not adhere to the wound itself due to the inherent moisture of wounds.

Likewise, dressings which cover catheters are generally known. The catheter may be inserted at a site on the patient and the site may be covered by the dressing. A window, or transparent film, may be provided within the dressing. The window may have an adhesive layer which may adhere to the patient. As a result, a caregiver may encounter difficulty in removing the dressing when the dressing must be replaced. In addition, known dressings may be rigid and may not conform to a shape of a catheter. As a result, an opening may be created between the dressing and an area being treated. The opening may allow contaminants to enter the area.

A need, therefore, exists for a dressing for an intravenous catheter site and a method for applying the same which may be flexible and may have an adhesive-free window to enable removal of the dressing from the catheter site without inadvertent adhesion to the patient and/or the catheter.

SUMMARY OF THE INVENTION

The present invention generally relates to a dressing and a method for applying the same to a site, such as, for example, a catheter site. The dressing may have a window, or transparent film, within the dressing which may allow an individual to view the a catheter entry point on a patient. The window may be free from adhesive, which may enable the dressing to be removed from the catheter without inadvertent adhesion to the patient and/or the catheter. Further, the dressing may be flexible and may contour to a shape of a catheter to prevent contaminants from entering an area of the patient which may be receiving treatment.

To this end, in an embodiment of the present invention, a dressing is provided which covers a site. The dressing has a transparent film layer having a top side and a bottom side. The dressing also has a site-contacting layer having a top side and a bottom side wherein the top side of the site-contacting layer is adjacent to the bottom side of the transparent film layer. The dressing further has an opening in the site-contacting layer wherein the opening enables viewing of the site when the site-contacting layer is on the site and further wherein a portion of the film layer covers the opening. In addition, the dressing has an adhesive layer between the transparent film layer and the site-contacting layer wherein the adhesive layer contacts the transparent film layer but does not contact the portion which covers the opening.

In an embodiment, the dressing has a top layer attached to the top side of the transparent film layer wherein the top layer surrounds the opening.

In an embodiment, the dressing has a securing tab adjacent to the transparent film layer wherein the securing tab has an adhesive layer.

In an embodiment, the dressing has a release liner in contact with the site-contacting layer wherein the release liner is removably attached to the site-contacting layer.

In an embodiment, the dressing has an adhesive layer in contact with the bottom side of the site-contacting layer.

In an embodiment, the dressing has an inlet formed within the site-contacting layer wherein the inlet extends toward the opening.

In an embodiment, the transparent film layer is moisture/vapor permeable.

In an embodiment, the site-contacting layer is absorbent.

In another embodiment of the present invention, a dressing is provided for covering a site. The dressing has a film layer. The dressing also has a site-contacting layer adjacent to the film layer wherein the film layer and the site-contacting layer form a window through which the site is viewed when the site-contacting layer covers the site. In addition, the dressing also has an adhesive between the film layer and the site-contacting layer wherein the adhesive does not contact the window.

In an embodiment, the dressing has a second film layer contacting the film layer wherein the film layer and the second film layer are removably adhered by surface tension between the film layer and the second film layer.

In an embodiment, the dressing has a top layer attached to the film layer wherein the top layer surrounds the window.

In an embodiment, the dressing has a release liner adjacent to the site-contacting layer wherein the release liner has a top side and a bottom side wherein the top side and the bottom side have a silicone coating.

In another embodiment of the present invention, a dressing is provided for covering a site. The dressing has a top layer having a length defined between a first end and a second end wherein the top layer has a top side and a bottom side wherein the top side is non-adhesive. The dressing also has a film layer having a top side and a bottom side wherein the film layer is adjacent to the bottom side of the top layer and further wherein the film layer has a length which is less than the length of the top layer. In addition, the dressing has a site-contacting layer having a top side and a bottom side wherein the top side of the site-contacting layer is attached to the bottom side of the film layer. Further, the dressing has an opening in the site-contacting layer enabling viewing of the site when the site-contacting layer is in contact with the site and further wherein the film layer covers the opening. The dressing also has an adhesive layer between the film layer and the site-contacting layer wherein the adhesive layer contacts the film layer but does not contact the film layer within the opening.

In an embodiment, the dressing has a first release liner and a second release liner attached to the site-contacting layer wherein the first release liner and the second release liner overlap.

In an embodiment, the first end and the second end of the top layer extend beyond the length of the film layer.

In an embodiment, the first end and the second end of the top layer extend beyond the site-contacting layer.

In an embodiment, the dressing has an adhesive layer between the film layer and the top layer.

In an embodiment, the dressing has an adhesive layer contacting the bottom side of the site-contacting layer.

In an embodiment, the dressing has an opening in the top layer wherein the opening is aligned with the opening in the site-contacting layer.

In another embodiment of the present invention, a dressing is provided for covering a site. The dressing has a top layer having a length defined between a first end and a second end wherein the top layer has a top side and a bottom side and wherein the top side is non-adhesive. The dressing also has a first film layer having a length which is less than the length of the top layer wherein the film layer is adjacent to the top layer. In addition, the dressing has a second film layer between the top layer and the first film layer wherein the second film layer and the first film layer are removable adhered by surface tension. The dressing also has a site-contacting layer having a length which is less than the length of the top layer wherein the site-contacting layer is adjacent to the first film layer and further wherein the film layer and an opening in the site-contacting layer form a window through which the site is viewed when the site-contacting layer covers the site. Further, the dressing has an adhesive layer between the first film layer and the site-contacting layer wherein the adhesive layer does not contact the window.

In an embodiment, the dressing has an adhesive layer between the top layer and the second film layer.

In an embodiment, the dressing has a first release liner and a second release liner removably attached to the site-contacting layer wherein the first release liner and the second release liner overlap.

In an embodiment, the top layer extends beyond the first film layer.

In an embodiment, the dressing has an opening within the top layer wherein the window is viewed through the opening.

In an embodiment, the dressing has an adhesive layer adjacent to the site-contacting layer wherein the adhesive layer contacts the site when the site-contacting layer covers the site.

In another embodiment of the present invention, a method is provided for applying a dressing to a site. The method comprises the steps of: providing a film layer adjacent to an site-contacting layer wherein an opening exists within the site-contacting layer and further wherein the film layer and the opening form a window to enable viewing of the site and further wherein a release liner is removably attached to the site-contacting layer; applying an adhesive layer between the film layer and the site-contacting layer wherein the adhesive layer contacts the film layer but does not contact the window; removing the release liner from the site-contacting layer; and placing the dressing on the site.

In an embodiment, the method has the further step of placing a catheter between the dressing and the site.

In an embodiment, the site is a catheter entry point.

It is, therefore, an advantage of the present invention to provide a dressing and a method for applying the same which may cover a catheter site.

Another advantage of the present invention is to provide a dressing and a method for applying the same wherein the dressing has a window which may allow viewing of a catheter entry point.

Another advantage of the present invention is to provide a dressing and a method for applying the same wherein the dressing may be removed without inadvertent adhesion to a patient and/or a catheter.

Further, an advantage of the present invention is to provide a dressing and a method for applying the same wherein the dressing is flexible.

A still further advantage of the present invention is to provide a dressing and a method for applying the same wherein the dressing has securing tabs which may be removed from the dressing and applied to a catheter to secure the catheter in a desired position.

Another advantage of the present invention is to provide a dressing and a method for applying the same wherein the dressing is inexpensive to manufacture.

Yet another advantage of the present invention is to provide a dressing and a method for applying the same wherein a label on the dressing provides patient identification and/or information.

Another advantage of the present invention is to provide a dressing and a method for applying the same wherein the dressing has an inlet to allow a catheter to be inserted between the dressing and an area receiving treatment.

Additional features and advantages of the present invention are described in, and will be apparent from, the detailed description of the presently preferred embodiments and from the drawings.

BRIEF DESCRIPTION OF THE DRAWINGS

FIG. 1 illustrates a top plan view of a dressing in an embodiment of the present invention.

FIG. 2 illustrates a side view of the dressing of FIG. 1 in an embodiment of the present invention.

FIG. 3 illustrates a side view of a dressing in an embodiment of the present invention.

DETAILED DESCRIPTION OF THE PRESENTLY PREFERRED EMBODIMENTS

The present invention generally relates to a dressing and a method for applying the same to a catheter site. The dressing may have a window, or transparent film, within the dressing which may allow an individual to view an entry point on a patient. The window may be free from adhesive, which may enable the dressing to be removed without inadvertent adhesion of the dressing to the patient and/or a catheter.

Referring now to the drawings wherein like numerals refer to like parts, FIG. 1 illustrates a dressing 2 of the present invention. The dressing 2 may have a left side 4, a right side 6 and a center portion 8. The dressing 2 may also have a top layer 42 which may surround the center portion 8. The top layer 42 may be constructed from, for example, paper, film, foil, or like material. The top layer 42 may also extend to the left side 4 and/or the right side 6 underneath securing tabs 20 (described below). The top layer 42 may have a width 12 which is less than a width 14 of a release liner 16, or backing.

The securing tabs 20 may be present on the left side 4 and/or the right side 6 and may be constructed from, for example, non-woven polyester, polyethylene foam, spun bonded nylon, polyurethane foam, absorptive cellulosic, or like material. The securing tabs 20 may have an adhesive layer (not shown) which enables adhesion to the top layer 42. In an embodiment, the top layer 42 may have a silicone coating (not shown) to allow removal of the securing tabs 20. A section 24 of the securing tabs 20 may be non-adhered to enable a user to grip one or more of the securing tabs 20 and remove the securing tab 20 from the dressing 2. In an embodiment, either of the securing tabs 20 may be removed from the dressing 2 and may be placed across, for example, a catheter or tubing. The adhesive layer on the securing tabs 20 may enable the securing tabs 20 to secure a catheter in a desired position at the catheter site.

A film layer 70, illustrated in FIG. 2, may be adjacent to the top layer 42. The film layer 70 may be constructed from, for example, polyethylene, polyester, polyethylene polyester blends, or like materials. An adhesive layer 44 may exist between the film layer 70 and the top layer 42. The adhesive layer 44 may be constructed from acrylic adhesive, silicone adhesive, synthetic rubber, or like adhesive bonding agents.

A non-adhesive layer 50 may be adjacent to the film layer 70. The non-adhesive layer 50 may be constructed from, for example, moisture/vapor permeable polyurethane. In an embodiment, the non-adhesive layer 50 may be a co-polyester film. A site-contacting layer 46, illustrated in FIG. 1, may be adjacent to the non-adhesive layer 50. The site-contacting layer 46 may be constructed from non-woven polyester, polyethylene foam, spun bonded nylon, polyurethane foam, absorptive cellulosic, or like material. In an embodiment, the site-contacting layer 46 may be absorbent. The dressing 2 may have a window 26 which may allow an individual to view, for example, a wound or catheter entry point when the dressing 2 is applied. The window 26 may be formed by the non-adhesive layer 50 and an opening 27 within the site-contacting layer 46. In an embodiment, the opening 27 may have, for example, a substantially semicircular shape. Adjacent to the window 26 may be an inlet 28 created along the center portion 8. In an embodiment, an individual may apply the dressing 2 at a catheter entry point. A catheter may be inserted between the dressing 2 and the entry point via the inlet 28. Moreover, inlet 28 may enable the dressing 2 to contour to a shape of the catheter.

FIG. 2 illustrates a cross-section of the dressing 2 along the line II—II. The top layer 42 may have a top side 43 and a bottom side 45. Adjacent to the bottom side 45 of the top layer 42 may be the adhesive layer 44. The adhesive layer 44 may have a top side 47 and a bottom side 49. The film layer 70 may be adjacent to the adhesive layer 44 and may have a top side 72 and a bottom side 74. Adjacent to the bottom side 74 of the film layer 70 may be a temporary adhesive layer 76 which may be constructed from, for example, an acrylic adhesive, a silicone adhesive, synthetic rubber, or like adhesive bonding agents. The adhesive used for the adhesive layer 76 may be a low-tack adhesive which is non-pressure sensitive. As a result, the film layer 70 may adhere to non-adhesive layer 50 due to surface tension between the film layer 76 and the non-adhesive layer 50. Accordingly, the film layer 70 may be separated from the non-adhesive layer 50 when the dressing 2 is applied at the site. The non-adhesive layer 50 may extend across the center portion 8. Adjacent to a bottom side 51 of the non-adhesive layer 50 may be an adhesive layer 52 which may be constructed from materials similar to those used for manufacture of the adhesive layer 44. The adhesive layer 52 may be present on the left side 4 and/or the right side 6. Moreover, the adhesive layer 52 may not contact the non-adhesive layer 50 in a section 31 which may contact the window 26. The site-contacting layer 46 may have a top side 61 which may contact a bottom side 63 of the adhesive layer 52. The site-contacting layer 46 may extend across the center portion 8. A top side 65 of an adhesive layer 54 may contact a bottom side 67 of the site-contacting layer 46. The adhesive layer 54 may be, for example, of a medical grade used for, for example, skin contact. The release liner 16 may be in contact with a bottom side 69 of the adhesive layer 54. The release liner 16 may have a silicone coating on a top side 17 and/or a bottom side 19. The silicone coating may enable removable attachment of, for example, a label to the release liner 16. The label may be attached to the top side 17 or the bottom side 19. The label may contain, for example, patient information. In general, each of the layers 42, 44, 46, 50 and 52 may have any dimensions which may enable securement, visibility and/or fluid management of a wound.

To apply the dressing 2 to a site, such as, for example, a catheter entry point of a patient, an individual or caregiver may remove the release liner 16 from the dressing 2 to expose the adhesive layer 54. The dressing 2 may then be applied over the entry point wherein the site-contacting layer 46 is in contact with the patient. The window 26 may allow viewing of the entry point and/or the patient. The adhesive layer 76 may have a weaker adhesion to the non-adhesive layer 50 than the adhesion of adhesive layer 54 to the site. As a result, the top layer 42, adhesive layer 44 and the film layer 70 may be removed. The non-adhesive layer 50, site-contacting layer 46, adhesive layer 52 and adhesive layer 54 may then remain attached at the site.

FIG. 3 illustrates a dressing 100 in another embodiment of the present invention. The dressing 100 may have a border layer 102 which may be constructed from, for example, film, such as, for example, polyurethane film or co-polyester film, or like material. The border layer 102 may have a top side 103 and a bottom side 105. The border layer may have an opening 133 which may enable viewing of a window (not shown) which may be created by a film layer 106 and an opening, represented by space 135, in a site-contacting layer 110. The border layer 102 may be, for example, permeable or semi-permeable. A top side 107 of an adhesive layer 104 may be in contact with the bottom side 105 of the border layer 102. The adhesive layer 104 may be constructed from, for example, an acrylic or like material which may be of a medical grade type adhesive. Adjacent to the adhesive layer 104 may be the film layer 106 having a top side 109 and a bottom side 111. The film layer 106 may be constructed from, for example, a clear non-adhesive film. In an embodiment, the film layer 106 may have a thickness 171 within a range of 0.5 mm to 3 mm. However, in other embodiments, the film layer 106 may have any thickness 171 which may provide an ability to view a wound as well as, for example, sealing of the wound from contaminants. The film layer 106 may have a length 127 which may be less than an overall length 129 of the dressing 100.

A top side 113 of an adhesive layer 108 may be in contact with the film layer 106. The adhesive layer 108 may be constructed from, for example, an acrylic or like material. The adhesive layer 108 may not contact the film layer 106 within a section 137 aligned with the space 135. Adjacent to a bottom side 115 of the adhesive layer 108 may be the site-contacting layer 110 having a top side 117 and a bottom side 119. The site-contacting layer 110 may be constructed from, for example, non-woven polyester, rayon, a polyester/rayon blend, a polyester/rayon/cotton blend, cotton, hydrophilic hydrogel, hydrophilic foam, polyethylene foam, spun bonded nylon, colloid-based adhesive, polyurethane foam, absorptive cellulosic, or like material. A top side 121 of an adhesive layer 112 may be in contact with the bottom side 119 of the site-contacting layer 110. The adhesive layer 112 may be similar in structure to the adhesive layer 104 or 108. Adjacent to the adhesive layer 112 may be release liners 114a, 114b which may overlap. A top side 123 of the release liner 114b may contact a bottom side 125 of release liner 114a. A top side 139 and/or the bottom side 125 of release liner 114a may be constructed from, for example, a silicone coated or polyethylene coated material. Likewise, the top side 123 and/or a bottom side 141 of release liner 114b may be constructed from, for example, a silicone coated or polyethylene coated material. The silicone coated or polyethylene coated material may enable removable adhesion of a label to the release liner 114a and/or the release liner 114b. The label may contain, for example, patient information. In general, each of the layers 102, 104, 106, 108, 110, 112, 114a and 114b may have any dimensions which may enable securement, visibility and/or fluid management of a wound.

To apply the dressing 100 to a catheter site, an individual or caregiver may peel each of the release liners 114a, 114b to expose the adhesive layer 112. The dressing 100 may then be applied over the catheter site wherein the site-contacting layer 110 is in contact with the patient. The section 137 of the film layer 106 may remain non-adhered to the patient and/or the catheter. The border layer 102 may extend beyond the film layer 106 and/or the adhesive layers 108, 112 and/or the site-contacting layer 110. As a result, an individual or caregiver may grip the border layer 102 to remove the dressing 100 from the site to, for example, treat the wound, or replace the dressing 100.

The dressings 2, 100 may have an adhesive contacting a film layer; however, the adhesive may not contact a window within the dressings 2, 100. As a result, the window may not be adhered to, for example, a wound or other portion of an individual. Thus, the dressings 2, 100 may be removed from a site without discomfort to a patient due to adherence of the window to the patient and/or the catheter. The materials from which the dressings 2, 100 are constructed may allow the dressings 2, 100 to be flexible when applied to a site. Accordingly, the dressings 2, 100 may contour to a shape of a catheter placed at a site and may reduce an amount of space between the site and the dressing 2, 100. Accordingly, contaminants may be prevented from entering the sited.

In addition, the dressings 2, 100 may have any variation of layers. Dressing configurations may depend on a type of treatment for an individual or patient. Preferred configurations may be those which enable securement, visibility and/or fluid management of a site. In an embodiment, each individual dressing 2, 100 may be packaged separately wherein the packaging may enable the dressing to be sterile prior to use. In another embodiment, two or more of the dressings 2, 100 may be placed within the same packaging.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A dressing for covering a site, the dressing comprising:
a first film layer having a top side and a bottom side wherein the first film layer is transparent;
a second film layer having a top side and a bottom side wherein the bottom side of the second film layer is removably adhered to the top side of the first film layer;
a paper layer attached to the top side of the second film layer;
a site-contacting layer having a top side and a bottom side wherein the top side of the site-contacting layer is adjacent to the bottom side of the first film layer;
an opening in the site-contacting layer, the second film layer and the paper layer wherein the opening enables viewing of the site when the site-contacting layer is on the site and further wherein a portion of the first film layer covers the opening; and
an adhesive layer between the first film layer and the site-contacting layer wherein the adhesive layer contacts the first film layer but does not contact the portion which covers the opening.

2. The dressing of claim 1 further comprising:
a top layer attached to the second film layer wherein the top layer surrounds the opening.

3. The dressing of claim 1 further comprising:
a securing tab adjacent to the first film layer wherein the securing tab has an adhesive layer.

4. The dressing of claim 1 further comprising:
a release liner in contact with the site-contacting layer wherein the release liner is removably attached to the site-contacting layer.

5. The dressing of claim 1 further comprising:
an adhesive layer in contact with the bottom side of the site-contacting layer.

6. The dressing of claim 1 further comprising:
an inlet formed within the site-contacting layer wherein the inlet extends toward the opening.

7. The dressing of claim 1 wherein the first film layer is moisture/vapor permeable.

8. The dressing of claim 1 wherein the site-contacting layer is absorbent.

9. A dressing for covering a site, the dressing comprising:
a first film layer having a top side and a bottom side;
a second film layer having a top side and a bottom side wherein the bottom side of the second film layer is removably adhered to the top side of the first film layer;
a site-contacting layer adjacent to the first film layer wherein the first film layer, the second film layer and the site-contacting layer form a window through which the site is viewed when the site-contacting layer covers the site;
a paper layer adhered to the top side of the second film layer wherein the paper layer surrounds the window; and
an adhesive between the first film layer and the site-contacting layer wherein the adhesive does not contact the window.

10. The dressing of claim 9 wherein the first film layer and the second film layer are removably adhered by surface tension between the first film layer and the second film layer.

11. The dressing of claim 9 further comprising:
a top layer attached to the second film layer wherein the top layer surrounds the window.

12. The dressing of claim 9 further comprising:
a release liner adjacent to the site-contacting layer wherein the release liner has a top side and a bottom side wherein the top side and the bottom side have a silicone coating.

13. A dressing for covering a site, the dressing comprising:
   a top layer having a length defined between a first end and a second end wherein the top layer has a top side and a bottom side wherein the top side is non-adhesive;
   a film layer having a top side and a bottom side wherein the top side of the film layer is removably attached to the bottom side of the top layer and further wherein the film layer has a length which is less than the length of the top layer;
   a paper layer adhered to the top side of the top layer;
   a site-contacting layer having a top side and a bottom side wherein the top side of the site-contacting layer is attached to the bottom side of the film layer;
   an opening in the site-contacting layer and the paper layer enabling viewing of the site when the site-contacting layer is in contact with the site and further wherein the film layer covers the opening; and
   an adhesive layer between the film layer and the site-contacting layer wherein the adhesive layer contacts the film layer but does not contact the film layer within the opening.

14. The dressing of claim 13 further comprising:
   a first release liner and a second release liner attached to the site-contacting layer wherein the first release liner and the second release liner overlap.

15. The dressing of claim 13 wherein the first end and the second end of the top layer extend beyond the length of the film layer.

16. The dressing of claim 13 wherein the first end and the second end of the top layer extend beyond the site-contacting layer.

17. The dressing of claim 13 further comprising:
   an adhesive layer between the film layer and the top layer.

18. The dressing of claim 13 further comprising:
   an adhesive layer contacting the bottom side of the site-contacting layer.

19. The dressing of claim 13 further comprising:
   an opening in the top layer wherein the opening is aligned with the opening in the site-contacting layer.

20. A dressing for covering a site, the dressing comprising:
   a top layer having a length defined between a first end and a second end wherein the top layer has a top side and a bottom side and wherein the top side is non-adhesive;
   a first film layer having a length which is less than the length of the top layer wherein the film layer is adjacent to the top layer;
   a second film layer between the top layer and the first film layer wherein the second film layer and the first film layer are removable adhered by surface tension;
   a site-contacting layer having a length which is less than the length of the top layer wherein the site-contacting layer is adjacent to the first film layer and further wherein the first film layer and an opening in the site-contacting layer form a window through which the site is viewed when the site-contacting layer covers the site; and
   an adhesive layer between the first film layer and the site-contacting layer wherein the adhesive layer does not contact the window.

21. The dressing of claim 20 further comprising:
   an adhesive layer between the top layer and the second film layer.

22. The dressing of claim 20 further comprising:
   a first release liner and a second release liner removably attached to the site-contacting layer wherein the first release liner and the second release liner overlap.

23. The dressing of claim 20 wherein the top layer extends beyond the first film layer.

24. The dressing of claim 20 further comprising:
   an opening within the top layer wherein the window is viewed through the opening.

25. The dressing of claim 20 further comprising:
   an adhesive layer adjacent to the site-contacting layer wherein the adhesive layer contacts the site when the site-contacting layer covers the site.

26. A method for applying a dressing to a site, the method comprising the steps of:
   providing a first film layer adjacent to a site-contacting layer wherein an opening exists within the site-contacting layer and further wherein the first film layer and the opening form a window to enable viewing of the site and further wherein a release liner is removably attached to the site-contacting layer;
   providing a second film layer having a top side and a bottom side wherein the bottom side of the second film layer is removably adhered to the first film layer;
   attaching a paper layer to the top side of the second film layer;
   applying an adhesive layer between the first film layer and the site-contacting layer wherein the adhesive layer contacts the first film layer but does not contact the window;
   removing the release liner from the site-contacting layer; and
   placing the dressing on the site.

27. The method of claim 26 further comprising the step of:
   placing a catheter between the dressing and the site.

* * * * *